US00PP24412P3

(12) United States Plant Patent
Willems

(10) Patent No.: US PP24,412 P3
(45) Date of Patent: Apr. 29, 2014

(54) *HAWORTHIA* PLANT NAMED 'CAPETOWN'

(50) Latin Name: *Haworthia fasciata*
Varietal Denomination: CAPETOWN

(75) Inventor: Rogier Willems, Tielen (BE)

(73) Assignee: Wander-Tuinier BV, Krimpen a/d Ijssel (NL)

( * ) Notice: Subject to any disclaimer, the term of this patent is extended or adjusted under 35 U.S.C. 154(b) by 115 days.

(21) Appl. No.: 13/507,698

(22) Filed: Jul. 20, 2012

(65) Prior Publication Data

US 2014/0026274 P1 Jan. 23, 2014

(51) Int. Cl.
*A01H 5/00* (2006.01)

(52) U.S. Cl.
USPC ..... Plt./263.1; Plt./226

(58) Field of Classification Search
None
See application file for complete search history.

(56) References Cited

U.S. PATENT DOCUMENTS

PP22,241 P3 * 11/2011 Lock ..... Plt./373

* cited by examiner

*Primary Examiner* — Wendy C Haas

(57) ABSTRACT

A new and distinct *Haworthia* cultivar named 'CAPETOWN' is disclosed, characterized by unique dotted leaves, top and underside. The new variety has strong roots and faster than normal growth rate. The new variety is a *Haworthia*, normally produced as an outdoor garden or container plant.

1 Drawing Sheet

Latin name of the genus and species: *Haworthia fasciata.*
Variety denomination: 'CAPETOWN'.

BACKGROUND OF THE INVENTION

The new *Haworthia* cultivar is a product of a planned breeding program conducted by the inventor, Rogier Willems, in Tielen, Belgium. The objective of the breeding program was to produce new *Haworthia* varieties for ornamental commercial applications. The cross resulting in this new variety was made approximately at an unidentifiable date, before 2008.

The seed parent is a unpatented, unnamed, proprietary seedling variety of *Haworthia fasciata*. The pollen parent is unknown, as the crossing resulting in 'CAPETOWN' was an open pollination, with unidentifiable pollen parents. The new variety was discovered in July 2008 by the inventor in a group of seedlings resulting from the crossing, in a research greenhouse in Tielen, Belgium.

Asexual reproduction of the new cultivar 'CAPETOWN' by tissue culture and vegetative cuttings was first performed at a research greenhouse in Tielen, Belgium in July 2008 and has shown that the unique features of this cultivar are stable and reproduced true to type in successive generations.

SUMMARY OF THE INVENTION

The cultivar 'CAPETOWN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAPETOWN' These characteristics in combination distinguish 'CAPETOWN' as a new and distinct *Haworthia* cultivar:

1. White dots on upper and lower side of leaves.
2. Stronger roots than typical of *Haworthia.*
3. Faster growth rate.

Plants of the new cultivar 'CAPETOWN' are similar to plants of the seed parent in most horticultural characteristics, however, plants of the new cultivar 'CAPETOWN' produce leaves with white spots on top and white dots on the underside, whereas the seed parent produces whites stripes top and underside of the leaf. 'CAPETOWN' also has stronger roots and a faster growth rate than the seed parent.

COMMERCIAL COMPARISON

Plants of the new cultivar 'CAPETOWN' are similar to plants of other known commercial *Haworthia fasciata* varieties in most horticultural characteristics. However, from the inventor's information, 'CAPETOWN' is the only variety producing the particular pattern of white dots on the upper and lower foliage surfaces. 'CAPETOWN' also has stronger roots and higher growth rate than other *Haworthia fasciata* varieties known to the inventor.

BRIEF DESCRIPTION OF THE PHOTOGRAPH

The accompanying photograph in FIG. 1 illustrates in full color a typical plant of 'CAPETOWN' grown in a greenhouse, in a 13 cm pot. Age of the plant photographed is approximately 11 months from a rooted cutting.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2005 except where general terms of ordinary dictionary significance are used. The following observations and measurements describe 'CAPETOWN' plants grown in a greenhouse in Tielen, Belgium. The growing temperature ranged from 18° C. to 28° C. during the day and from 13° C. to 18° C. during the night. General light conditions are bright, normal sunlight. Measurements and numerical values represent averages of typical plant types. Plants are approximately 11 months old from a rooted plantlet.

Botanical classification: *Haworthia fasciata* 'CAPETOWN'.

PROPAGATION

Time to initiate roots: About 70 days at approximately 20-28° C.

Root description: Moderately thick, moderately branched, slightly fibrous, slightly fleshy, colored near RHS Greyed-Yellow 161C.

Propagation method: Vegetative divisions or tissue culture.

PLANT

Growth habit: Upright, from basal rosettes.

Height: Approximately 12.3 cm to top of highest leaf.

Plant spread: Approximately 18.7 cm.

Growth rate: Moderate.

Branching characteristics: No main or lateral branches, plant consists of basal rosette.

FOLIAGE

Leaf:

*Arrangement.*—Basal rosette.

*Average length.*—Approximately 9.8 cm.

*Average width.*—Approximately 1.5 cm (measured at ⅓ from the base).

*Shape of blade.*—Narrow lanceolate, straight.

*Apex.*—Narrow acute.

*Base.*—Broad cuneate.

*Margin.*—Entire.

*Texture of top surface.*—Pustulate.

*Texture of bottom surface.*—Pustulate, in axillary bands.

*Quantity of leaves per plant.*—Approximately 125.

*Color.*—Young foliage upper side: Near RHS Green N137A, base lighter; Yellow-Green 145A, leaf covered with small dots (pustulate), colored near RHS White N155D. Young foliage under side: Near RHS Green N137B, base lighter; Yellow-Green 145B, leaf covered with small dots (pustulate) connected to axillary stripes, coloured near RHS White N155D. Mature foliage upper side: A color in between RHS Green N137D and 147A, base lighter; Green N137D, leaf covered with small dots (pustulate), coloured near RHS White N155D. Average diameter of dots: 1 mm. Mature foliage under side: Near RHS Green N137A, base lighter; N137D, leaf covered with small dots (pustulate) connected to axillary stripes, coloured near RHS NN155D. Average width of stripes: 1.8 mm, stripes are placed approximately 3 mm apart from each other.

*Venation.*—Type: Linear. Venation color upper side: A color in between RHS N137D and 147A, base lighter; N137D. Venation color under side: Near RHS N137A, lighter at the base; N137D.

FLOWER

No flowers observed to date.

OTHER CHARACTERISTICS

Seeds and fruits: No seed or fruit observed to date.

Disease/pest resistance: Neither resistance nor susceptibility to diseases and pests has been observed.

Temperature tolerance: Tolerates temperatures from approximately 5° C. to 45° C.

What is claimed is:

1. A new and distinct cultivar of *Haworthia* plant named 'CAPETOWN' as herein illustrated and described.

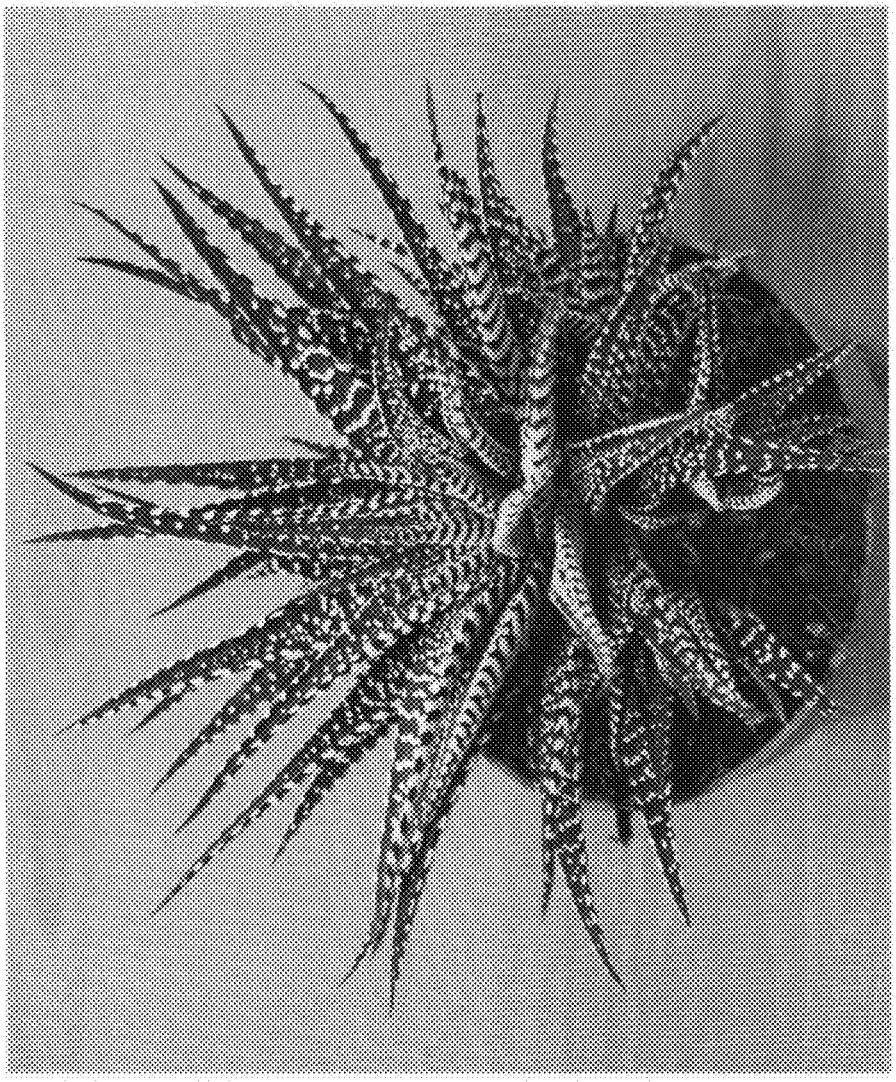

* * * * *